US008431751B1

(12) United States Patent
Castillo et al.

(10) Patent No.: US 8,431,751 B1
(45) Date of Patent: Apr. 30, 2013

(54) POLYMERIC QUATERNARY AMMONIUM COMPOUNDS WITH VICINAL HYDROXY GROUPS

(75) Inventors: Ernesto J. Castillo, Fort Worth, TX (US); Hwang-Hsing Chen, Fort Worth, TX (US); Masood A. Chowhan, Arlington, TX (US); Glenn D. Stafford, Jr., White Settlement, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 374 days.

(21) Appl. No.: 12/644,069

(22) Filed: Dec. 22, 2009

Related U.S. Application Data

(60) Provisional application No. 61/140,713, filed on Dec. 24, 2008.

(51) Int. Cl.
*C07C 205/00* (2006.01)
*C08G 61/00* (2006.01)
*C08G 73/00* (2006.01)

(52) U.S. Cl.
USPC ............................. 568/704; 528/397; 528/422

(58) Field of Classification Search .................. 568/704; 528/397, 422
See application file for complete search history.

(56) References Cited

U.S. PATENT DOCUMENTS

| 3,931,319 A * | 1/1976 | Green et al. .................. 564/286 |
| 4,001,432 A | 1/1977 | Green et al. |
| 4,012,446 A | 3/1977 | Green et al. |
| 4,027,020 A * | 5/1977 | Green et al. ............. 514/217.03 |
| 4,407,791 A | 10/1983 | Stark |
| 4,525,346 A | 6/1985 | Stark |
| 5,342,620 A | 8/1994 | Chowhan |
| 5,505,953 A | 4/1996 | Chowhan |
| 5,512,597 A | 4/1996 | Kyba et al. |
| 5,631,005 A | 5/1997 | Dassanayake et al. |
| 5,811,466 A | 9/1998 | Chowhan et al. |
| 6,143,799 A | 11/2000 | Chowhan et al. |
| 6,319,464 B1 | 11/2001 | Asgharian |
| 6,365,636 B1 | 4/2002 | Chowhan et al. |
| 6,503,497 B2 | 1/2003 | Chowhan et al. |
| 6,528,048 B1 | 3/2003 | Koike et al. |
| 6,664,294 B1 | 12/2003 | Park et al. |
| 6,849,253 B2 | 2/2005 | Chowhan et al. |

FOREIGN PATENT DOCUMENTS

| EP | 1 656 955 A1 | 5/2006 |
| GB | 536017 | 4/1941 |
| WO | 90/02555 | 3/1990 |
| WO | 98/47359 | 10/1998 |

OTHER PUBLICATIONS

Houlsby et al. (Antimicrobial Agents and Chemotherapy, vol. 29, No. 5, Published May 1986, pp. 803-806).*
Codling et al. (Journal of Antimicrobial Chemotherapy, 51, Published 2003, pp. 1153-1158).*
Schmidt et al., 1980, Chemische Berichte, vol. 113, issue 5, p. 1691-1707.
Seebach D. and Daum H, 1974, Chemische Berichte, vol. 107, issue 5, p. 1748-1763.

* cited by examiner

*Primary Examiner* — Richard Schnizer
*Assistant Examiner* — Alma Pipic
(74) *Attorney, Agent, or Firm* — Michael Rein

(57) ABSTRACT

New polymeric quaternary ammonium compounds with vicinal hydroxyl groups are disclosed. These compounds are useful as disinfectants in contact lens care compositions and/or as preservatives in ophthalmic compositions. Compositions containing these compounds are also disclosed. These compositions are especially useful for disinfecting/cleaning contact lenses.

19 Claims, No Drawings

POLYMERIC QUATERNARY AMMONIUM COMPOUNDS WITH VICINAL HYDROXY GROUPS

CROSS REFERENCE TO RELATED APPLICATION

This application claims priority under 35 U.S.C. §119 to U.S. Provisional Patent Application No. 61/140,713, filed Dec. 24, 2008, the entire contents of which are incorporated herein by reference.

FIELD OF THE INVENTION

The present invention is directed to new polymeric quaternary ammonium compounds with vicinal hydroxyl groups. The invention is also directed to the use of these new compounds as disinfecting agents in lens care compositions and/or as preserving agents in ophthalmic, otic or nasal compositions.

BACKGROUND OF THE INVENTION

Pharmaceutical formulations used for treating the eyes, ears or nose typically require preservation to prevent their contamination with potentially harmful microorganisms. For this purpose specially selected antimicrobial agents are added to the formulations as preservatives. The antimicrobial agents used are normally expected to exhibit sufficient biocidal activity so as to preclude the harboring of microorganisms. Similarly, formulations used for the care, cleaning and disinfection of contact lenses must be able to exert antimicrobial activity against those microorganisms likely to contaminate such lenses. A number of small organic molecules have been used as preservatives and disinfectants in ophthalmic lens care formulations, for example, compounds such as benzalkonium chloride (BAC), chlorhexidine, and thimerosal.

Benzalkonium choroide (BAK, BAC) is a member of a class of compounds known as quaternary ammonium compounds, Quats or QACs. This class also includes compounds such as cetyl trimethylammonium bromide (CTMB), cetylpyridinium chloride (Cetrim), cetylpyridinium chloride (CPC) and benzethonium chloride (BZT). Benzalkonium chloride is a mixture of alkylbenzyl dimethylammonium chlorides of various alkyl chain lengths. The greatest bactericidal activity is associated with the C12-C14 alkyl derivatives. Benzalkonium chloride has been used commercially as a disinfectant and spemicide in a wide variety of products, for example, hand and face washes, mouthwashes, spermicidal creams, to name just a few, as well as in various formulations useful for treating the eye or nose.

While potent in regard to antimicrobial activity, practitioners have become aware over the years of the potential for some of these small organic antimicrobial agents to be toxic to sensitive tissues, for example, to the cornea of the eye. In addition, some of these small molecules have been found to accumulate in contact lenses, particularly in soft, hydrophilic contact lenses. As these compounds may leach from the lenses while they are worn in the eye, the sensitive tissues of the eye may be repeatedly exposed to these agents which can cause additional irritation and possible damage and irritation to the cornea.

For their potential in overcoming some of the disadvantages of the smaller organic, monomeric compounds described above, polymeric quaternary ammonium compounds have been investigated for a number of years.

For example, British Patent No. 536,017 (Aug. 30, 1941), assigned to E. I. DuPont de Nemours (the "DuPont Patent"), discloses linear polymeric quaternary ammonium compounds and methods for their preparation. The compounds of the DuPont Patent were envisioned to be useful in photographic processing, to treat leather, as mold inhibitors and pesticides, and as modifying agents. There is, however, no mention of use of these compounds as disinfectants or preservatives in pharmaceutical products.

U.S. Pat. Nos. 3,931,319 (Jan. 6, 1976), 4,001,432 (Jan. 4, 1977) and 4,012,446 (Mar. 15, 1977), all issued to Green, et al., disclose a group of high molecular weight "capped" linear polymeric quaternary ammonium compounds found to be effective microbiocides (antimicrobials). The Green, et al. compounds are "capped" in the sense that both ends of the chains terminate in quaternary ammonium moieties. In a continuation-in-part application, now U.S. Pat. No. 4,027,020 (May 31, 1977), Green, et al. disclose a process for making randomly capped linear polymeric quaternary ammonium compounds; that is, the polymers produced by the improved process include those with very short chain lengths as well as those having relatively long chain lengths. These compounds were also found to have antimicrobial activity.

U.S. Pat. Nos. 4,407,791 (Oct. 4, 1983) and 4,525,346 (Jun. 25, 1985), both issued to Stark, disclose disinfecting solutions for contact lenses, wherein the aqueous solutions contain the Green, et al. polymers, including the compound polyquaternium-1, commercially known as Onamer M® or PolyQuad®.

Practitioners involved with developing formulations for use in lens care or ophthalmic compositions for ocular use recognize that there are many trade-offs and choices to be made in developing a particular formulation. In the case of biocidal compounds, for example, it is often found that the more potent biocide is also more toxic to sensitive ocular tissues. Certain agents may also show differential selectivity in activity, is for example, showing a greater or lower level of antibacterial activity against particular microorganisms, or class of microorganisms, e.g., Gram-positive or Gram-negative bacteria, or fungi, e.g., *C. Albicans*. While in some applications a broad spectrum of activity is desirable, in others a selective activity may be preferred, for example, where the practitioner desires to boost the activity of an existing formulation against a particular microorganisms or class or microorganism.

When optimizing a particular formulation, in addition to demonstrating biocidal activity against a suitable range of microorganisms, there are also several additional factors to consider; for example, mutual compatibility of formulation constituents, relative availability and/or raw material cost, and, in the case of lens care formulations, contact lens uptake, and so on. More recently, increasing concern for the implications of biocide accumulation in the environment, and also the phenomena of antimicrobial resistance are among the new factors to consider when selecting a particular preserving agent.

Considering these challenges, a preservative and/or disinfection agent which has effective antimicrobial activity, preferably across a range of microorganisms, and which also is not toxic and/or damaging to the cornea or other mucosal tissues, does not cause irritation to the sensitive tissues of the eye, ear or nose, and is also comfortable to use would be highly desirable. In addition, a preservative which is compatible with the articles of its intended use as well as with other formulation components would be likewise desirable. Finally, a preservative which is readily degraded into non-toxic and biologically inactive products after its intended purpose has been achieved in vivo, as well as in the environment, would likewise be considered highly advantageous. The present invention is directed to satisfying one or more of these needs.

SUMMARY OF THE INVENTION

The present invention is directed to new polymeric quaternary ammonium compounds. In particular, the present invention relates to new polymeric quaternary ammonium compounds which contain vicinal hydroxyl groups, and compositions containing these compounds. The present invention also relates to the use of these compounds as disinfecting and/or preserving agents in pharmaceutical and lens care products. In particular, the present invention relates to the use of these new compounds as preservatives for ophthalmic, otic or nasal compositions and/or as disinfectants for contact lens care products. It has now been found that the compounds of the present invention are particularly suited for these purposes, having demonstrated, for example, antimicrobial activity.

The compounds of the present invention differ from prior compounds through the introduction of vicinal hydroxyl chemical groups. Without wishing to be bound by theory, it is thought that the increase in chain hydrophilicity which the vicinal hydroxy groups impart may act to 'soften' the physiological impact of these compounds on sensitive tissues of the eye, ear and/or nose, thereby increasing patient comfort and tolerance. The vicinal hydroxy groups of the compounds of the present invention can facilitate unique interactions with other formulation constituents. For example, the compounds of the present invention may form reversible complexes with borate thereby acting to decrease absorption of the compounds into contact lenses or to advantageously alter the viscosity of the compositions and/or their antimicrobial activity. Finally, the introduction of vicinal hydroxyl chemical groups may also act to provide greater chemical lability, and thereby compounds of the present invention may be more readily degraded into nontoxic and biologically inactive products in vivo, as well as in the environment.

Other features and advantages of the invention will become apparent from the following detailed description and claims.

DETAILED DESCRIPTION OF THE INVENTION

As utilized herein, the following terms, unless otherwise indicated, shall be understood to have the following meanings:

For purposes of this specification, disinfectants, biocides and/or preservatives shall be collectively referred to as "antimicrobials" and compounds having biocidal, disinfecting and/or preserving efficacy shall be referred to as compounds having "antimicrobial activity." In addition, the terms "polymeric quaternary ammonium compounds" or "polymers" shall hereinafter refer to polymeric quaternary ammonium compounds and their pharmaceutically acceptable salts, and the terms shall be used interchangeably throughout this specification.

The term "alkyl" means a straight or branched chain hydrocarbon containing from 1-to-5 carbon atoms. Representative examples of alkyl include, but are not limited to, methyl, ethyl, n-propyl, iso-propyl, n-butyl, sec-butyl, iso-butyl, tert-butyl, n-pentyl, and the like.

The term "disinfecting amount" means an amount of an antimicrobial agent that achieves the desired effect of disinfecting contact lenses by substantially reducing the number of viable microorganisms present on the contact lens, preferably an amount which, either singly or in combination with one or more additional antimicrobial agents, is sufficient in achieving the desired effect.

The term "preservation-effective amount" means an amount of an antimicrobial agent that achieves the desired effect of preserving a composition from microbial contamination, preferably an amount which, either singly or in combination with one or more additional antimicrobial agents, is sufficient to satisfy the preservative efficacy requirements of the United States Pharmacopeia ("USP").

The term "ophthalmically acceptable vehicle" means a pharmaceutical composition having physical properties (e.g., pH and/or osmolality) that are physiologically compatible with ophthalmic tissues.

The term "pharmaceutically acceptable carrier" means a non-toxic material that is physiologically compatible with the tissues of the body. The characteristics of the carrier will depend on the route of administration. Optionally, the pharmaceutical carrier composition contains diluents, fillers, salts, buffers, stabilizers, solubilizers, antioxidants, preservatives and other materials which are conventionally used in pharmaceutical compositions.

The novel antimicrobial polymers of the present invention are those of formula (I), below:

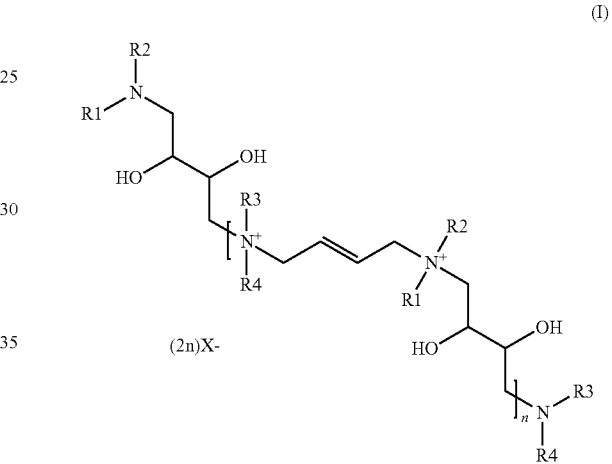

(I)

and pharmaceutically acceptable salts thereof, wherein:

X⁻ is a pharmaceutically acceptable anion, preferably a halide, more preferably chloride;

n is an integer from 2 to 1000, preferably from 10 to 70, more preferably from 30 to 50; and R1 and R2 are independently selected from the group consisting of alkyl having 1 to 5 carbon atoms, and isomers thereof.

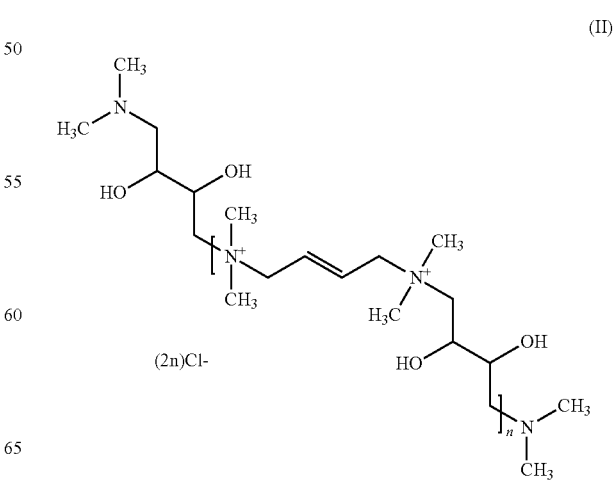

(II)

Preferred polymers of the present invention are those of Formula (II) wherein n is an integer from 10 to 70, more preferably from 20 to 60, most preferably from 30 to 50.

The polymers of the present invention may be characterized as heteropolymers or copolymers, as they are derived from two monomeric species. The polymers of the present invention can be made and purified by utilizing the methods of the DuPont or the Green, et al. patents to synthesize a polymeric mixture, then to separate the desired molecular weight fraction by chromatographic methods, by using dialysis membranes, by trituration, by a combination of these methods or by other means known to those skilled in the art of polymer separation and purification.

A general scheme for the preparation of the polymers of the present invention is depicted below, wherein a 1,4-bis(dialkylamino)ethane-2,3-diol is condensed with trans-1,4-dichloro-2-butene to form the polymers depicted in Formula (I).

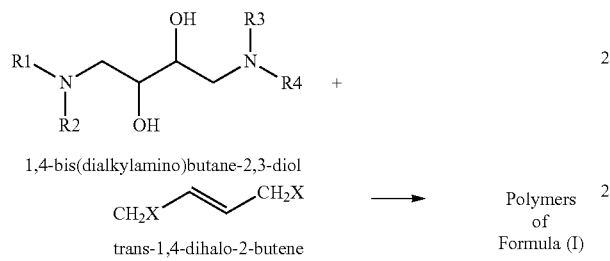

In this reaction, when there is a slight molar excess of the diol reactant, the polymerization proceeds until the trans-1,4-dihalo-2-butene is depleted, and the resulting polymers are terminated with the diol reactant. However, under conditions where the trans-1,4-dihalo-2-butene is in initial excess, the polymeric chains formed will have termini of active halogen atoms, and the ends of the chain will therefore be reactive toward the addition of more amine. In this case, an alternative monotertiary amine "capping" group can be added to form quaternized chain ends which are incapable of further reaction. Any number of monofunctional tertiary amines are suitable for this "capping" purpose, including, for example, triethanolamine, and others as described in U.S. Pat. No. 4,027,020 (Green et al.), the entire content of which is hereby incorporated into the present specification by reference.

In a preferred embodiment of the present invention, (2S,3S)-1,4-bis(dialkylamino)ethane-2,3-diol was used as one of the monomer reactants. (2S,3S)-1,4-bis(dialkylamino) ethane-2,3-diol was obtained from N,N,N',N'-tetramethyl-L-tartaramide, commercially available (Sigma-Aldrich, St. Louis Mo.), using a method described in Seebach, D. and Daum, H., in Chemische Berichte, Volume 107, Issue 5, pages 1748-1763. Other methods using alternative starting materials are also contemplated and are within the scope of the present invention. For example, using tartaric acid as the starting material, L-1,2,3,4-dianhydro-threitol may be prepared, and then reacted with a dimethylamine to form (2S,3S)-1,4-bis(dimethylamino)butaine-2,3-diol, according to a method described in Schmidt et al., Chemische Berichte, Volume 113, Issue 5, pages 1691-1707.

Ref 1

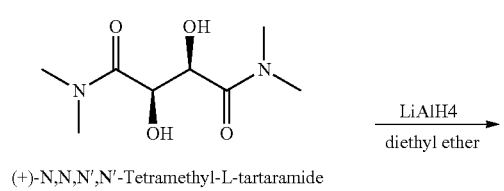

(+)-N,N,N',N'-Tetramethyl-L-tartaramide

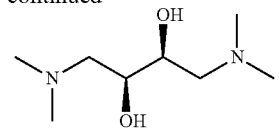

(2S,3S)-1,4-bis(dimethylamino)butane-2,3-diol

Ref 2

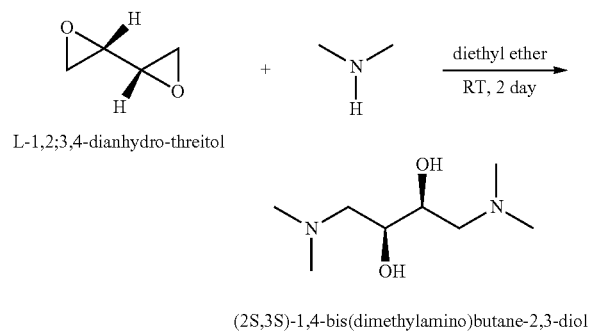

(2S,3S)-1,4-bis(dimethylamino)butane-2,3-diol

Alternatively, N,N,N',N'-tetramethyl-tartaramide or analogs thereof may be prepared using, for example, one of the readily available starting materials shown in synthetic approaches 1) and 2) shown below. Hydrogenation of the resulting diamides will provide the 1,4-bis(dialkylamino)butane-2,3-diol monomers for use in the preparation of the polymers of the present invention.

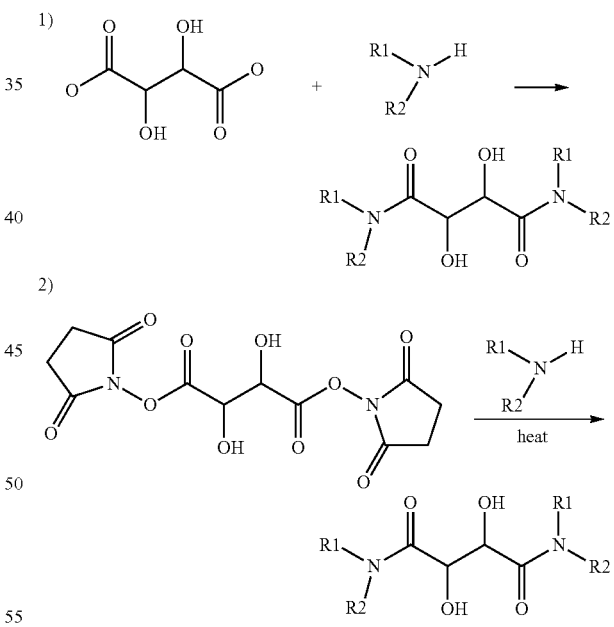

The polymers of the present invention may be used as antimicrobials in various compositions, particularly as disinfectants in contact lens care products and as preservatives in ophthalmic, nasal or otic compositions, and are especially suitable for use in ophthalmic compositions such as artificial tears or topical ophthalmic pharmaceutical preparations. The types of compositions which may be preserved by the compounds of formula (I) include: ophthalmic pharmaceutical compositions, such as those described below; otic pharmaceutical compositions, such as topical compositions used in the treatment of bacterial infections or inflammation of the ear; dermatological compositions, such as anti-inflammatory compositions, as well as shampoos and other cosmetic compositions; and various other types of pharmaceutical compositions. In general, the polymers of the present invention will be present in the compositions at a concentration between about 0.00001 and 1.0 percent by weight/volume percent (w/v %). If used as a disinfectant, the polymers are preferably present at a concentration of between about 0.0005 and 0.5 w/v %; if used as a preservative, the polymers are present at a concentration between about 0.00005 and 0.05 w/v %. It is preferred that the polymers are present at a concentration of between 0.001 and 0.05 w/v % if used as a disinfectant and between 0.0001 and 0.01 w/v % if used as a preservative.

The compositions of the present invention may additionally contain other components, for example, buffers, tonicity adjusting agents, chelating agents, surfactants, solubilizers, active pharmaceutical agents, preservatives, pH adjusting agents and carriers.

In the case of contact lens and ophthalmic solutions, for example, various agents are added to enhance compatibility with the eye. To avoid stinging or irritation it is important that the solution possess a tonicity and pH within the physiological range, e.g., 200-350 mOsmole for tonicity and 6.5-8.5 for pH. To this end, various buffering and osmotic agents are often added. The simplest osmotic agent is sodium chloride since this is a major solute in human tears. In addition propylene glycol, lactulose, trehalose, sorbitol, mannitol or other osmotic agents may also be added to replace some or all of the sodium chloride. Also, various buffer systems such as citrate, phosphate (appropriate mixtures of $Na_2HPO_4$, $NaH_2PO_4$, and $KH_2PO_4$), borate (boric acid, sodium borate, potassium tetraborate, potassium metaborate and mixtures), bicarbonate, and tromethamine and other appropriate nitrogen-containing buffers (such as ACES, BES, BICINE, BIS-Tris, BIS-Tris Propane, HEPES, HEPPS, imidazole, MES, MOPS, PIPES, TAPS, TES, Tricine) can be used to ensure a physiologic pH between about pH 6.5 and 8.5. Borate and polyol systems may also be used to provide buffering, to enhance antimicrobial activity, or to provide both buffering and an enhancement of antimicrobial activity, or other useful properties to the compositions of the invention. The borate and polyol systems which may be used include those described in U.S. Pat. Nos. 6,849,253; 6,503,497; 6365,636; 6,143,799; 5,811,466; 5,505,953; and 5,342,620; the entire contents of each are hereby incorporated into the present specification by reference.

The borates which may be used in the compositions of the present invention include boric acid and other pharmaceutically acceptable salts such as sodium borate (borax) and potassium borate. As used herein, the term "borate" refers to all pharmaceutically suitable forms of borates, as well as metaborates. Borates are common excipients in ophthalmic formulations due to good buffering capacity at physiological pH and well known safety and compatibility with wide range of drugs and preservatives.

In addition to the compounds of formula (I) described above, the compositions of the present invention may contain one or more additional antimicrobial agent. The invention is not limited relative to the types of additional antimicrobial agent that may be utilized. The preferred biocides include: polyhexamethylene biguanide polymers ("PHMB"), polyquaternium-1, and the amino biguanides described in U.S. Pat. No. 6,664,294, the entire contents of which are hereby incorporated in the present specification by reference.

Amidoamines, amino alcohols, and borate/polyol complexes may also be utilized to enhance the antimicrobial activity of the compositions described herein. The preferred amidoamines are myristamidopropyl dimethylamine ("MAPDA") and related compounds described in U.S. Pat. No. 5,631,005 (Dassanayake, et al.). The preferred amino alcohols are 2-amino-2-methyl-1-propanol ("AMP") and other amino alcohols described in U.S. Pat. No. 6,319,464 (Asgharian). The entire contents of the '005 and '464 patents are hereby incorporated in the present specification by reference.

The following examples further illustrate certain embodiments of the invention. These examples are provided to aid in the understanding of the invention and are not to be construed as limitations thereof.

Example 1: Synthesis

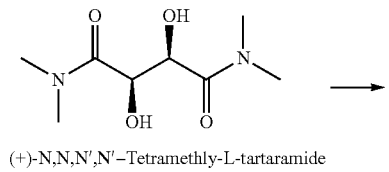

(+)-N,N,N',N'-Tetramethly-L-tartaramide

A

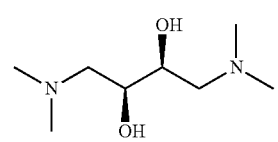

(2S,3S)-1,4-bis(dimethylamino)butane-2,3-diol

B

Preparation of compound B [(2S,3S)-1,4-bis(dimethylamino)butane-2,3-diol] from compound A [(+)-N,N,N',N'-Tetramethyl-L-tartaramide].

To a three-neck flask equipped with a condenser, flashed with nitrogen, cooled on an ice bath was added anhydrous ether (500 mL) and then lithium aluminum hydride (10.0 g, 263 mmol) slowly in about 10 min. To the stirred suspension was added compound A (20.0 g, 98.0 mmol) in portions over about 10 min. with caution (the reaction is exothermic and hydrogen gas is formed). The mixture was stirred for 30 min at ambient temperature and then heated at reflux overnight (about 18 h). A small aliquot was removed for analysis by LC/MS to confirm the completeness of the reaction. The reaction mixture was cooled on an ice bath and quenched very slowly by the addition of ethyl acetate (20 mL), water (9 mL), 15% NaOH (9 mL) and water (18 mL) successively with stirring. After 1 h additional ethyl acetate (600 mL) was added, stirred for 30 min and filtered over filter agent (Celite). The filtrate was concentrated to give a crude oil (12.31 g, 71%). The oil was fractionally distilled at 80-89° C. under high vacuum to give the desired compound B as an oil that solidified on standing. LC/MS (APCI+) 177 (M+H).

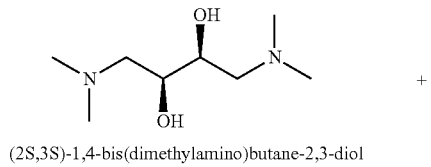

(2S,3S)-1,4-bis(dimethylamino)butane-2,3-diol

B

trans-1,4-dichloro-2-butene

C

Reaction of compound B and compound C [trans-1,4-dichloro-2-butene] to form polymers of formula (II).

2.8692 g C was added to a ground glass round bottom flask along with 40 mL of tetrahydrofuran. 4.2232 g B was added to a scintillation vial then rinsed into the reaction flask with 20 mL of tetrahydrofuran. Reaction mixture was heated for 1.25 hours at 50-60° C., then 40 mL of methanol was added because of the formation of a white precipitate. The precipitate dissolved upon addition of the methanol and the reaction mixture was heated for an additional 7 hours at 50-60° C. After the reaction was completed, there was observed a gel-like substance on the bottom, slightly hazy on the top. The decanted liquid was treated with 250 mL ethyl ether which produced a white emulsion.

The white substance was allowed to settle to the bottom and the ethyl ether was decanted off. The white substance was dried in a vacuum oven for 6 days at 40-45° C. The gel-like substance in the original reaction mixture was dissolved in 150 mL methanol then washed with 100 mL ethyl ether. This resulted in a white emulsion in the top layer and a light yellow rubbery substance on the bottom layer. The white emulsion layer was decanted off and the bottom layer was heated in a vacuum oven for 6 days at 40-45° C. Then 100 mL ethyl ether was added to the white emulsion layer, the white substance allowed to settle and the ethyl ether decanted off. Structures of both synthesized monomers and products were confirmed by NMR and Mass Spectrometry.

Example 2

Testing

One of the compounds of the present invention was evaluated for preservative activity using a Stand alone Test Procedure for Contact Lens Disinfecting Solutions (such as OPTI-FREE EXPRESS). The Stand Alone Test challenges a formulation with a standard inoculum of a representative range of microorganisms and establishes the extent of their viability loss at pre-determined time intervals comparable with those during which the formulation may be used. The test is based on guidelines and standards provided in the ISO 14729:2001 Standard: "Ophthalmic Optics-Contact Lens Care Products—Microbiological Requirements and Test Methods for Products and Regimens for Hygienic Management of Contact Lenses", and the FDA Guidelines: "Premarket Notification (510 k) Guidance Document for contact Lens Care Products (May, 1997)".

The test uses five test organisms (3 bacteria and 2 fungi): Bacteria: *Staphylococcus aureus, Pseudomonas aeruginosa, Serratia marcescens*, and fungi: *Candida albicans* (yeast) and *Fusarium solani* (mold). The testing described below was a Stand Alone Screen test (abbreviated Stand Alone test), using 3 organisms: *S. aureus, S. marcescens*, and *C. albicans*.

About $1^6$ (1 million) organisms were inoculated into 10 mL of the formulation being tested, mixed, and held at room temperature for 6 hours. Then, a 1 ml sample was withdrawn, diluted and plated with agar using a serial dilution pour-plate method. Both the dilution fluid and the agar contained neutralizing agents to stop the action of the antimicrobials. Then, the pour-plates (agar plates) were incubated at appropriate temperatures and times to recover the specific organisms being tested. After incubation, the agar plates were counted and recorded, and calculations were done to show the amount of kill or reduction of the numbers of organisms.

Example of calculations: Initial Inoculum level=1.0× $10^6$ (Log=6.0)

Count after 6 hrs=1.0×$10^3$(Log=3.0)

Log Reduction @6 hr=(6.0−3.0)=3.0 log reduction

The test solution was prepared according to the information presented in Table 1, using three lots of the compound of Formula (II): 05-39680, 05-39681 and 05-39682. The control 04-500618-1 was polyquaternium-1. The microbiological test results are shown in Table 2 below.

TABLE 1

| Formulation Component | Concentration (%) |
|---|---|
| Tetronic 1304 | 0.1 |
| ALDOX ® | 0.0005 + 7% xs |
| C9ED3A | 0.1 |
| Propylene Glycol | 1.0 |
| Sodium Borate (Decahydrate) | 0.115 |
| Sodium Chloride | 0.1 |
| Sodium Citrate (Dihydrate) | 0.83 |
| Formula (II) Compound or polyquaternium-1 | 0.001 |
| NaOH/HCl to adj. pH | 7.9 |
| Purified Water | QS to 100% |
| Final pH | 7.9 |

TABLE 2

| Lot | Microbe | Initial | 6 hours | 6 hours |
|---|---|---|---|---|
| 05-39680 | S. aureus | 1.0E+06 | 6.1E+05 | 0.2 |
| 05-39680 | P. aeruginosa | 1.3E+06 | 3.9E+02 | 3.5 |
| 05-39680 | S. marcescens | 8.2E+05 | 1.5E+05 | 0.7 |
| 05-39681 | S. aureus | 1.0E+06 | 5.7E+05 | 0.2 |
| 05-39681 | P. aeruginosa | 1.3E+06 | 6.0E+02 | 3.3 |
| 05-39681 | S. marcescens | 8.2E+05 | 1.7E+05 | 0.7 |
| 05-39682 | S. aureus | 1.0E+06 | 2.7E+05 | 0.6 |
| 05-39682 | P. aeruginosa | 1.3E+06 | 5.0E+01 | 4.4 |
| 05-39682 | S. marcescens | 8.2E+05 | 6.4E+04 | 1.1 |
| 04-500618-1 | S. aureus | 1.0E+06 | 2.6E+03 | 2.6 |
| 04-500618-1 | P. aeruginosa | 1.3E+06 | 1.3E+02 | 4.0 |
| 04-500618-1 | S. marcescens | 8.2E+05 | 3.2E+02 | 3.4 |

Example 3

Representative Preserved Contact Lens Disinfecting Formulation

| Ingredient | w/v % |
|---|---|
| Compound of Formula (I) | 0.001 |
| Sodium Citrate | 0.56 |
| Citric Acid | 0.021 |
| Sodium Chloride | 0.52 |
| EDTA | 0.05 |
| NaOH/HCl | pH 7 |
| Purified Water | q.s. |

Example 4

Representative Preserved Ophthalmic Formulation

| Ingredient | w/v % |
|---|---|
| Compound of Formula (I) | 0.001 |
| Polyoxyl 40 Stearate | 0.1 |

-continued

| Ingredient | w/v % |
|---|---|
| Boric Acid | 0.25 |
| Sodium Chloride | 0.75 |
| Disodium Edetate | 0.01 |
| NaOH/HCl | q.s., pH = 7.4 |
| Purified Water | q.s. 100% |

The composition above is prepared by the following method. The batch quantities of boric acid, sodium chloride, disodium edetate, and polyquaternium-1 are weighed and dissolved by stirring in 90% of the batch quantity of purified water. The pH is adjusted to 7.4.+−.0.1 with NaOH and/or HCl. Purified water is added to q.s. to 100%. The mixture is stirred for five minutes to homogenize and then filtered through a sterilizing filter membrane into a sterile recipient.

While the disclosure has been described with reference to a preferred embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from essential scope thereof. Therefore, it is intended that the disclosure not be limited to the particular embodiment disclosed as the best mode contemplated for carrying out this invention, but that the disclosure will include all embodiments falling within the scope of the appended claims.

We claim:
1. A polymer of formula:

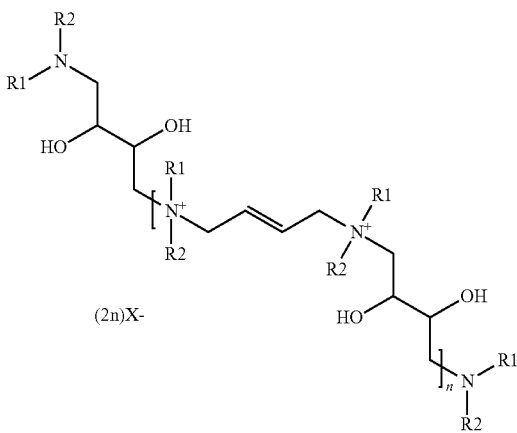

(2n)X− and pharmaceutically acceptable salts thereof, wherein:
X is a pharmaceutically acceptable anion;
n is an integer in the range of 2 to 1000;
R1 and R2 are the same or different and are selected from the group consisting of alkyl having from 1 carbon to 5 carbon atoms;
and isomers thereof, and wherein the polymer is capable of forming a reversible complex with borate.

2. The polymer according to claim 1 wherein n is in the range of 10 to 70.

3. The polymer according to claim 2 wherein R1 and R2 are each methyl and X is chloride.

4. A polymer characterized by a repeat unit having the formula

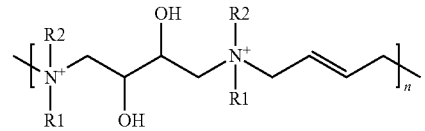

and pharmaceutically acceptable salts thereof, wherein:
X is a pharmaceutically acceptable anion;
R1 and R2 are the same or different and are selected from the group consisting of alkyl having from 1 carbon to 5 carbon atoms; and
n is an integer in the range of 2 to 1000, and wherein the polymer is capable of forming a reversible complex with borate.

5. A polymer comprising a condensation product of 1,4-dihalo-2-butene with a monomer of formula

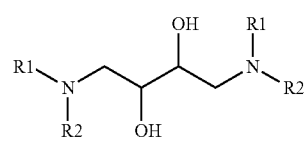

where R1 and R2 are the same or different and are selected from the group consisting of alkyl having from 1 carbon to 5 carbon atoms, wherein the polymer has vicinal hydroxy groups and is capable of forming a reversible complex with borate.

6. A pharmaceutical composition comprising a preservation-effective amount of a polymer according to claim 1.

7. The pharmaceutical composition according to claim 6, wherein the pharmaceutical composition further comprises an ophthalmically-acceptable vehicle.

8. The pharmaceutical composition according to claim 7, further comprising borate.

9. A lens care composition comprising a disinfecting amount of a polymer according to claim 1.

10. The lens care composition according to claim 9, further comprising borate.

11. A pharmaceutical composition comprising a preservation-effective amount of a polymer according to claim 4.

12. A pharmaceutical composition comprising a preservation-effective amount of a polymer according to claim 5.

13. A lens care composition comprising a disinfecting amount of a polymer according to claim 4.

14. A lens care composition comprising a disinfecting amount of a polymer according to claim 5.

15. The pharmaceutical composition according to claim 6, further comprising at least one additional antimicrobial agent.

16. The pharmaceutical composition according to claim 15, wherein the at least one additional antimicrobial agent is polyquaternium-1.

17. The lens care composition according to claim 9, further comprising at least one additional antimicrobial agent.

18. The lens care composition according to claim 17, wherein the at least one additional antimicrobial agent is polyquaternium-1.

19. A polymer comprising a condensation product of 1,4-dihalo-2-butene with a monomer of formula

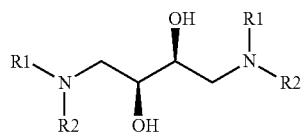
where R1 and R2 are the same or different and are selected from the group consisting of alkyl having from 1 carbon to 5 carbon atoms, wherein the polymer has vicinal hydroxy groups and is capable of forming a reversible complex with borate.
\* \* \* \* \*